(12) United States Patent
Prescott

(10) Patent No.: US 7,464,607 B2
(45) Date of Patent: Dec. 16, 2008

(54) SUTURE PULL-OUT TESTER AND METHOD OF USE

(75) Inventor: Michael R. Prescott, Hamden, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 288 days.

(21) Appl. No.: 11/410,828

(22) Filed: Apr. 24, 2006

(65) Prior Publication Data

US 2006/0283871 A1  Dec. 21, 2006

Related U.S. Application Data

(60) Provisional application No. 60/674,460, filed on Apr. 25, 2005.

(51) Int. Cl.
*G01N 3/08* (2006.01)
(52) U.S. Cl. .......................................... 73/826; 73/760
(58) Field of Classification Search ................... 73/826, 73/760
See application file for complete search history.

(56) References Cited

U.S. PATENT DOCUMENTS

| 5,366,081 | A | | 11/1994 | Kaplan et al. |
| 5,500,991 | A | * | 3/1996 | Demarest et al. .......... 29/407.08 |
| 5,918,284 | A | * | 6/1999 | Blanch et al. ................. 73/827 |
| 6,557,426 | B2 | * | 5/2003 | Reinemann et al. .... 73/862.393 |
| 6,730,013 | B1 | * | 5/2004 | Shank et al. .................... 600/7 |
| 7,343,791 | B2 | * | 3/2008 | Cuevas et al. ................. 73/160 |

OTHER PUBLICATIONS

European Search Report. Date: Jul. 8, 2006.

* cited by examiner

*Primary Examiner*—Max Noori

(57) ABSTRACT

A suture pull-out tester is disclosed which includes a load cell assembly, a drive track, a jig and a drive assembly. The load cell assembly has a force measuring device and an attachment member for retaining one end of a filament. The jig includes a receptacle dimensioned to receive a suture package. The jig is driven along the drive track by the drive assembly such that the attachment member draws the filament from the suture package. The force measuring device measures the forces required to withdraw the filament from the suture package.

23 Claims, 5 Drawing Sheets

SUTURE PULL-OUT TESTER AND METHOD OF USE

CROSS REFERENCE TO RELATED APPLICATION

The present application claims the benefit of and priority to U.S. Provisional Application Ser. No. 60/674,460 filed on Apr. 25, 2005, the entire contents of which are incorporated herein by reference.

TECHNICAL FIELD

The present disclosure relates to a device for measuring the force required to withdraw a filament from a container. More specifically, the present disclosure relates to a device for measuring the force required to withdraw a suture from a suture package.

BACKGROUND OF RELATE ART

Filament holders such as suture packages are well known. Typically, a suture package includes at least one suture with a needle attached thereto. The needle may be releasably retained within the suture package and the suture may be wound about structure within the package. When a surgeon requires a suture, the needle can be grasped by a forceps or by the hand and pulled to withdraw the suture from the package.

It is desirable that a suture withdraw easily and smoothly from a package without binding, snagging or becoming entangled. It is also desirable that a suture be positioned within a package such as not to be deformed to such an extent that the suture does not hang straight after being withdrawn from the suture package.

Currently, there is no effective device for testing a suture package to assure that the suture package configuration is such as to facilitate smooth and easy withdrawal of a suture from the suture package. Accordingly, it would be desirable to provide a device capable of measuring the force required to withdraw a suture from a suture package. Such a device would function to identify design flaws that exist in the construction of a suture package.

SUMMARY

A suture pull-out tester is disclosed which includes a load cell assembly, a drive track, a jig and a drive assembly. The load cell assembly includes a force measuring device and an attachment member. The attachment member communicates with the force measuring device and is adapted to retain one end of a filament housed within the suture package. The jig is movably supported on the drive track and is configured to support a suture package. The drive assembly is associated with the jig and is operative to move the jig along the drive track.

In one embodiment, the suture pull-out tester includes a frame which supports the load cell assembly, the drive track and the jig. The frame may define a three dimensional rectangular structure. In one embodiment, the load cell assembly and the drive track are movably mounted on the frame and the frame includes first, second and third transverse beams. The load cell assembly is supported between the first and second transverse beams and the drive track is supported between the second and third transverse beams. The drive track and the load cell assembly are supported on the transverse beams on runners. Each of the runners is slidably supported on a respective one of the first, second and third transverse beams.

In one embodiment, the force measuring device includes a mechanical transducer. The mechanical transducer may be in the form of a strain gauge. In one embodiment, the force measuring device is connected to a display device.

In one embodiment, the load cell assembly is supported on a support block and the support block is supported on the frame.

In another embodiment, the drive assembly is fluid driven, e.g., pneumatic, hydraulic, etc. Alternately, the drive assembly can include a screw drive mechanism or an induction drive mechanism.

In one embodiment, the jig includes a base member movably supported on the drive track and a suture package support member supported on the base member. The suture package support member can be pivotally mounted on the base member. In one embodiment, the suture package support member defines a receptacle dimensioned to receive a suture package. A clamp can be positioned within the receptacle to secure the suture package within the receptacle. The clamp can be urged by a biasing member from a rear wall defining the receptacle towards a front wall defining the receptacle to secure a suture package within the receptacle.

In one embodiment, the drive track is linear. Alternately, the drive track can be non-linear.

A method for measuring the forces required to withdraw a suture from a suture package is also disclosed. The method comprises the following steps:

i) providing a suture pull-out tester including a load cell assembly having a force measuring device and an attachment, a drive track, a jig and a drive assembly for advancing the jig along the drive track;

ii) supporting a suture package on the jig;

iii) attaching one end of a filament supported within the suture package to the attachment member of the load cell assembly;

iv) actuating the drive assembly to advance the jig along the drive track to withdraw the suture from the suture package at a controlled rate; and v) using the force measuring device of the load cell assembly to measure the tension in the filament during withdrawal of the filament from the suture package.

The force measuring device can be in the form of a strain gauge. Further, the step of providing can include providing a display device for translating signals from the force measuring device into usable data.

BRIEF DESCRIPTION OF THE DRAWINGS

Various embodiments of the presently disclosed suture pull-out tester are disclosed herein with reference to the drawings, where.

DETAILED DESCRIPTION OF EMBODIMENTS

Embodiments of the presently disclosed suture pull out tester will now be described in detail with reference to the drawings in which like numerals designate identical or corresponding elements in each of the several views.

Figure 1:
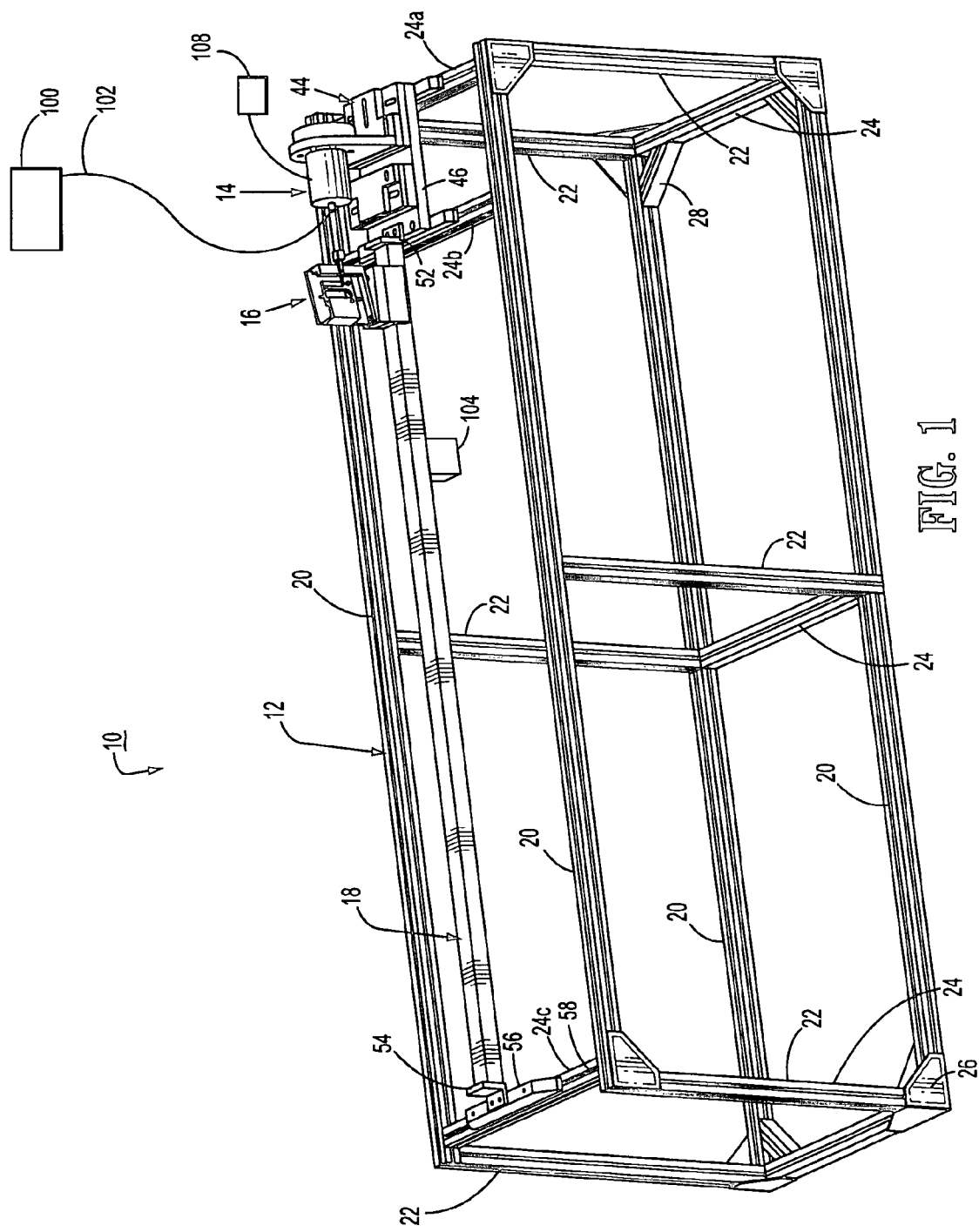
FIG. 1 is a side perspective view of one embodiment of the presently disclosed suture pull-out tester.

FIG. 1 illustrates one embodiment of the presently disclosed suture pull-out tester shown generally as 10. Briefly, suture pull out tester 10 includes a support frame 12, a load cell assembly 14, a nest or jig 16, and a drive track assembly 18. In one embodiment, support frame 12 supports load cell assembly 14 in an axially fixed position. Drive track assembly 18 extends along the length of frame 12 and slidably supports jig 16 such that jig 16 is movable in relation to load cell assembly 14.

In one embodiment, frame 12 includes a three dimensional rectangular support structure including a plurality of longitudinal beams 20, a plurality of vertical beams 22 and a plurality of transverse beams 24. Gussets 26 and corner support beams 28 are provided to provide additional stability to the structure. The plurality of transverse beams 24 include three upper transverse beams 24a, 24b and 24c which are positioned between upper longitudinal beams 20 at spaced locations along the length of longitudinal beams 20. Beams 24a and 24b are positioned to support load cell assembly 14 and beams 24b and 24c are positioned to support drive track assembly 18. Although frame 12 is illustrated as a three dimensional rectangular structure, it is envisioned that frame 12 may assume any of a variety of configurations capable of supporting load cell assembly 14, jig 16 and drive track assembly 18 in the manner to be discussed in further detail below. For example, load cell assembly 14, jig 16 and drive track assembly 18 can be supported on and/or mounted to a bench or table top supported on one or more support members, e.g., table legs.

Figure 2:
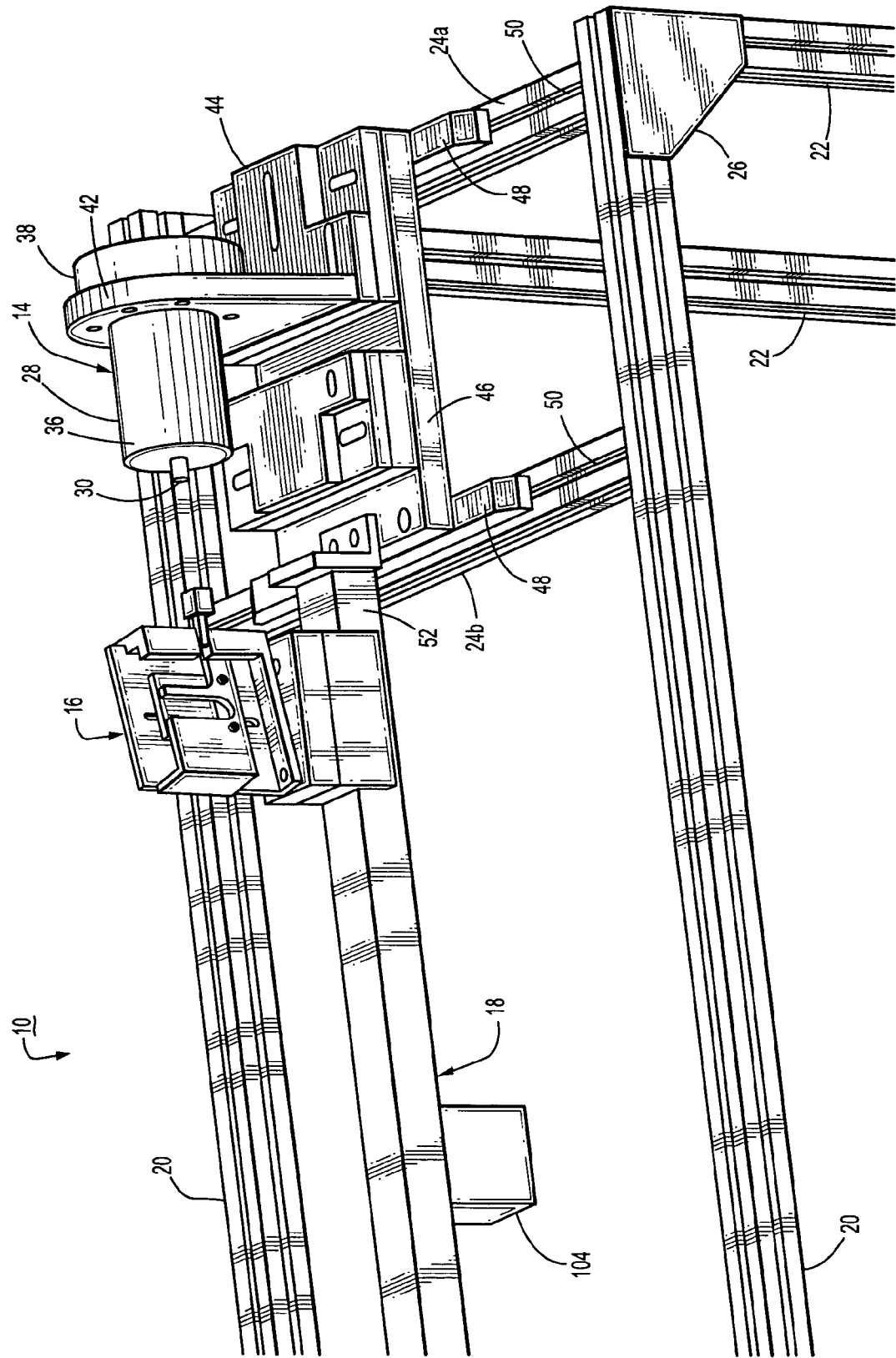
FIG. 2 is an enlarged side perspective view of one end of the suture pull-out tester shown in FIG. 1 illustrating the load cell assembly, the jig and a portion of the frame and drive track assembly.
Figure 2A:
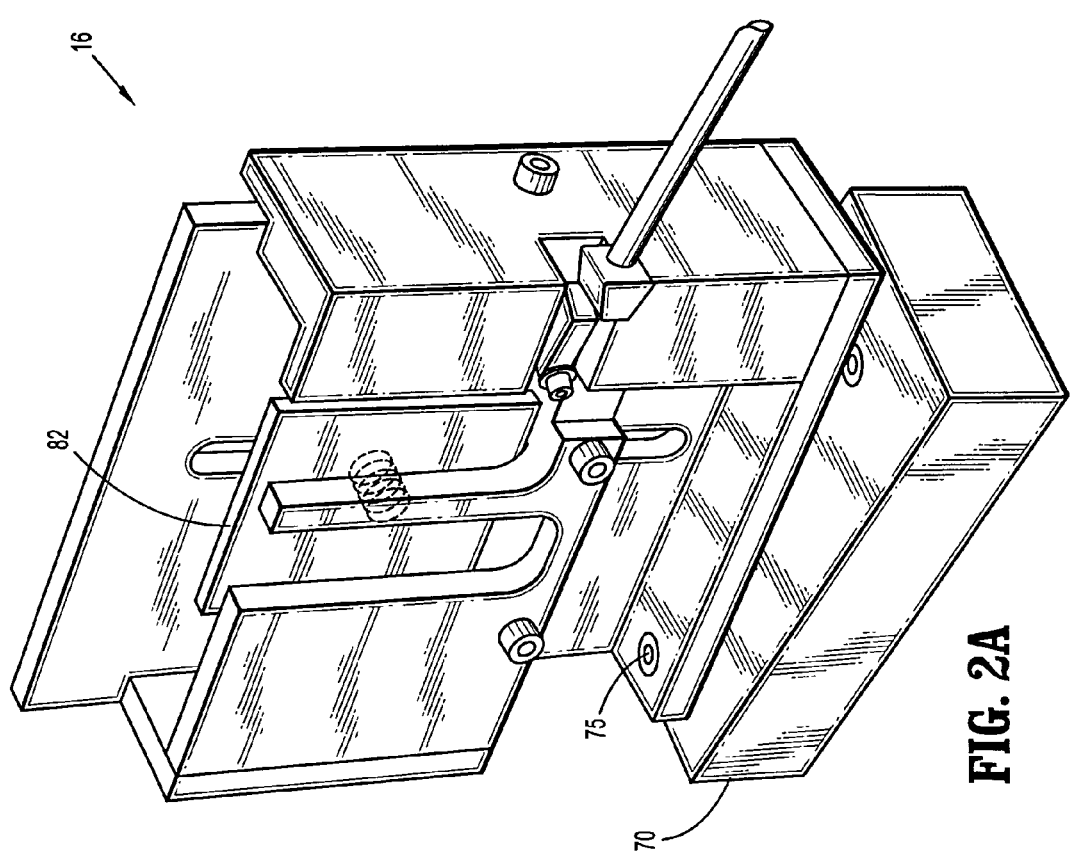
FIG. 2A is an enlarged side perspective view of the jig of the suture pull-out tester shown in FIG. 2.

Referring also to FIG. 2, load cell assembly 14 includes a housing 28 and a finger or attachment member 30. Attachment member 30 may include a slot, recess or the like for receiving one end of a suture. Alternately, attachment member 30 may define structure to which a suture can be tied. In one embodiment, housing 28 is cylindrical and is dimensioned to receive one or more force measuring devices 108 shown schematically in FIG. 1. Although force measuring device 108 is shown schematically positioned externally of housing 28, force measuring device 108 is positioned within housing 28. The force measuring devices may be electromechanical transducers which are operably connected to finger 30. In this device, the electromechanical transducers may be strain gauges as will be discussed in more detail below. The electromechanical transducers are attached by electrical cables 102 to a measuring or readout/display device 100 such as known in the art. The display device translates signals received from the force measuring devices into usable data.

In one embodiment, housing 28 of load cell assembly 14 includes a stepped body portion including a distal portion 36 and a proximal portion 38. Proximal portion 38 has a diameter which is larger than distal portion 36. Distal portion 36 is dimensioned to be received within an opening in a support flange 42 of a support block assembly 44 to fixedly secure housing 28 of load cell assembly 14 to support block assembly 44. Distal portion 36 of housing portion 28 can be secured to support flange 42 using any known fastening technique, e.g., friction, welding, screws, etc.

Support block assembly 44 includes a base plate 46. Base plate 46 is secured to a pair of spaced runners 48. In one embodiment, runners 48 are slidably mounted on transverse beams 24a and 24b to facilitate transverse movement of load cell assembly 14 on frame 12. Each transverse beam 24a and 24b may include an undercut track or slot 50 for receiving a projection (not shown) formed on runners 48 to prevent base plate 46 from becoming disengaged from frame 12. The projection may be of a dovetail configuration and the slot 50 may be configured to receive the dovetail configuration. Alternately, other interlocking configurations may be employed. A set screw or the like (not shown) may also be provided to secure runners 48 at a fixed position along transverse beams 24a and 24b of frame 12.

Figure 3:
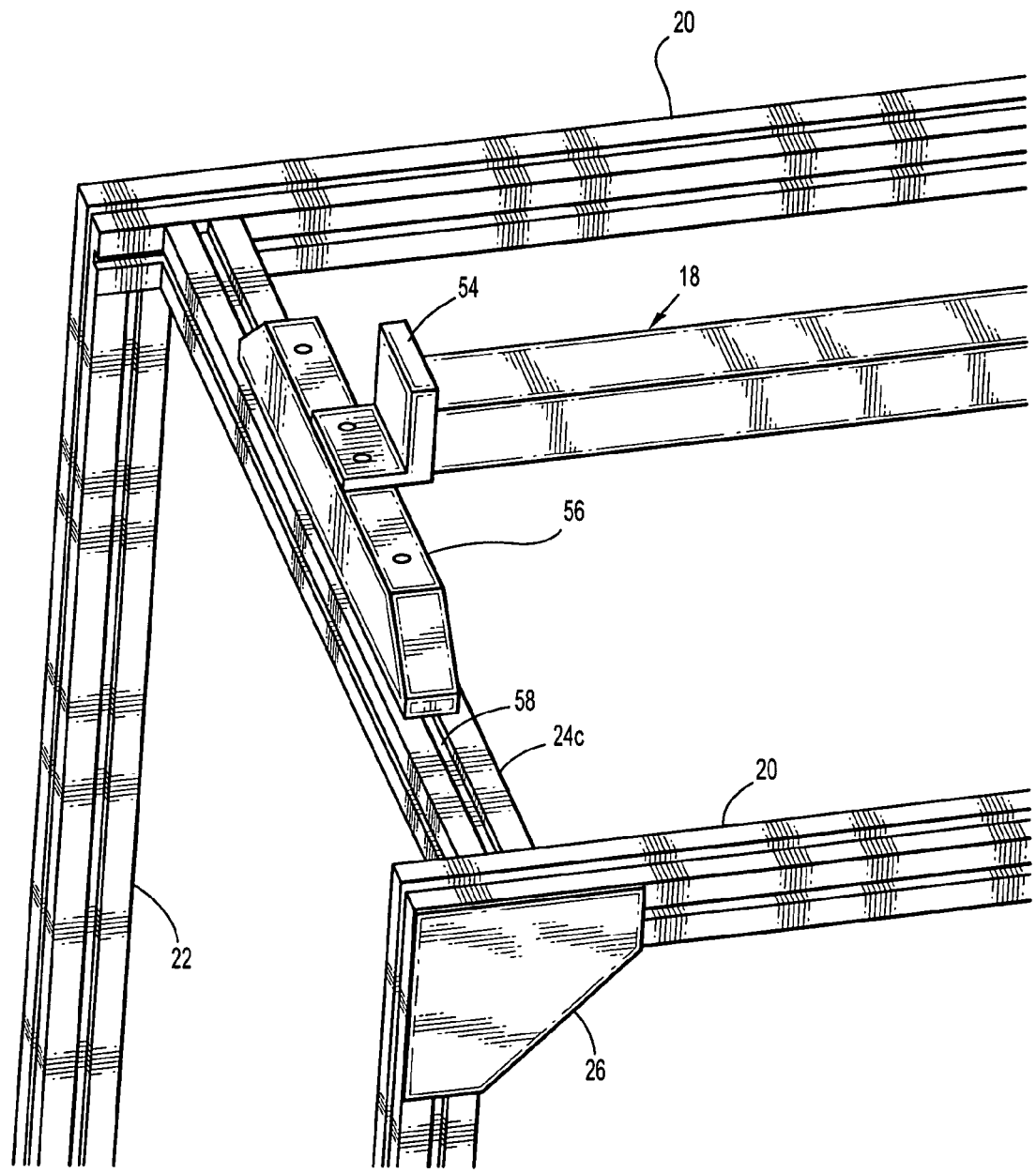
FIG. 3 is an enlarged side perspective view of the other end of the suture pull-out tester shown in FIG. 1 illustrating another portion of the frame and drive track assembly.

Referring also to FIG. 3, drive track assembly 18 includes a first end fastened to a bracket 52 supported on base plate 46 of support block assembly 44 and a second end fastened to a bracket 54 supported on a runner 56. Runner 56 is slidably supported on transverse beam 24c. As discussed above with respect to runners 48, runner 56 may include a projection (not shown), e.g., dovetail shape, which is configured to be received within an undercut track or slot 58 formed in transverse beam 24c. Runners 48 and 56 facilitate transverse positioning or repositioning of load cell assembly 14 and drive track assembly 18 on frame 12. It is also envisioned that the load cell assembly 14 and drive track assembly 18 can be fixedly attached to frame 12.

Figure 4:
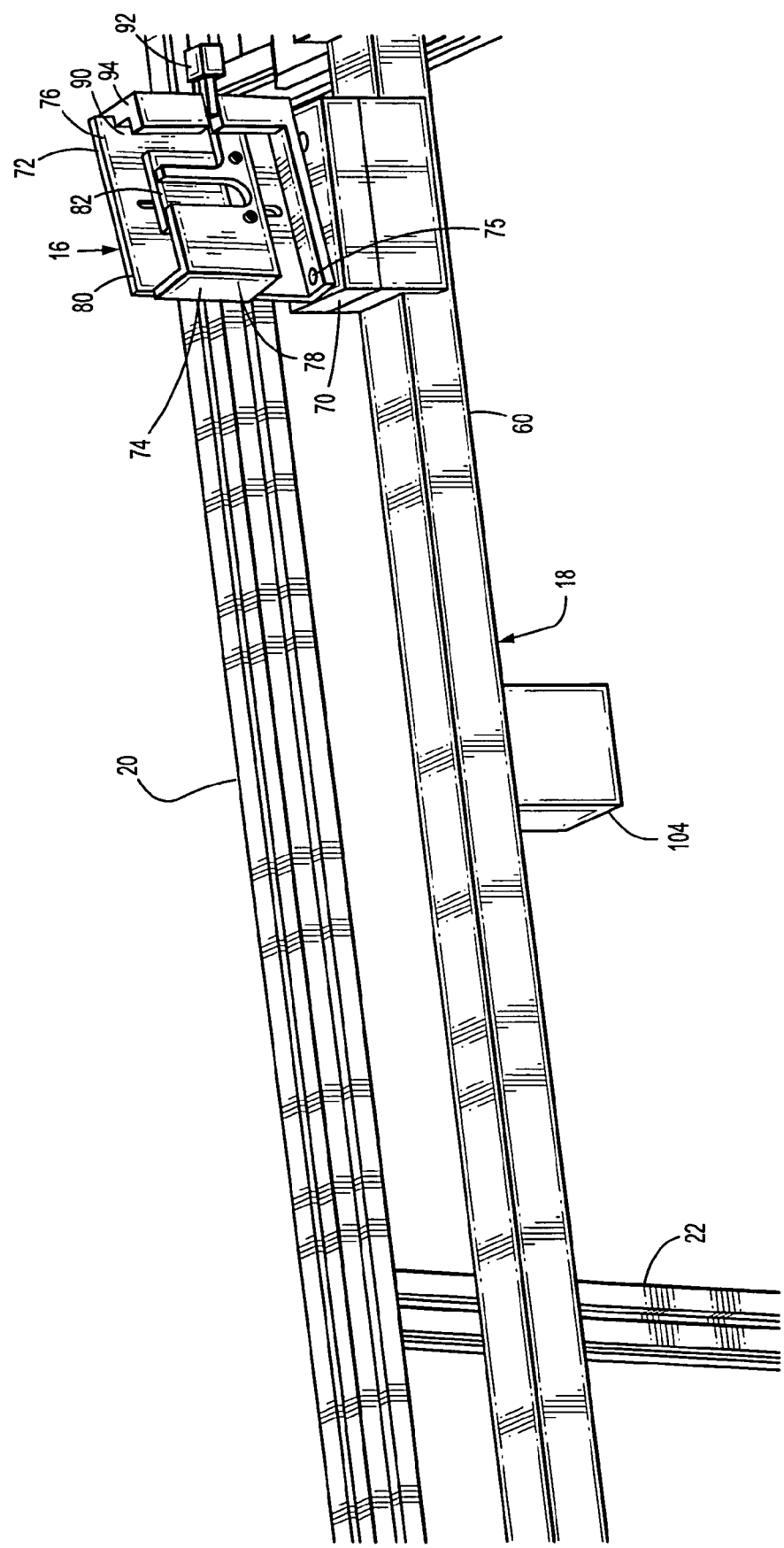
FIG. 4 is an enlarged side perspective view of the jig and a portion of the frame and drive track assembly of the suture pull-out tester shown in FIG. 1.

Referring also to FIG. 4, drive track assembly 18 includes a track 60 upon which jig 16 is slidably mounted. Drive track assembly 18 also includes a drive mechanism 104 for effecting movement of jig 16 along track 60. Drive mechanism 104 is shown schematically in FIG. 1. In one embodiment, the drive mechanism is constructed to advance jig 16 at a rate of between 10 to 25 inches per second. In another embodiment, the drive mechanism is constructed to advance jig 16 at a rate of 12 to 20 inches per second. It is envisioned that other speeds of advancement may also be desired, e.g., 5 in/sec., 50 inches/sec., etc.

Track 60 may define a hollow channel for receiving a piston (not shown). The piston can be operably connected to jig 16 such that when the piston is driven through track 60, jig 16 is advanced along track 60. The piston may be fluid driven, i.e., air, water, oil, etc., as is known in the art. In another embodiment, the drive mechanism may include a servo driven belt drive system which is operably connected to jig 16 to advance jig 16 along track 60. A servo driven belt drive system provides the added benefit of allowing accurate stopping of jig 16 at any point along track 60. It is also contemplated that other types of drive mechanisms may be used to advance jig 16 along track 60, e.g., screw drive mechanisms, induction drive mechanisms, etc.

As shown in FIG. 4, jig 16 includes a base member 70 which is slidably supported on track 60 and a suture package support member 72. Suture package support member 72 includes a housing 74 which is pivotally supported on base member 70 about a pivot member 75. Support member 72 defines a receptacle 76 for receiving a suture package. In one embodiment, receptacle 76 is defined by spaced front and rear walls 78 and 80. A clamp 82 is supported on rear wall 80 and is urged toward front wall 78 by a biasing member (not shown) positioned between rear wall 80 and clamp 82. The biasing member may be in the form of a coil spring or the like. Clamp 82 is urged from rear wall 80 towards front wall 78 to clamp a suture package between clamp 82 and front wall 78 and retain a suture package within receptacle 76.

In another embodiment, clamp 82 is replaced by a carrier member (not shown) which is configured to be removably received snugly within receptacle 76. The carrier member includes a concavity or recess for receiving a suture package. It is envisioned that a plurality of carrier members, e.g., support blocks, may be provided, wherein each carrier member defines a concavity dimensioned and configured to receive a differently sized and/or configured suture package. As such, suture pull out tester 10 can be used to test suture packages of all different types and sizes.

Front wall 78 includes a cutout 90 formed therethrough. Cutout 90 is positioned to facilitate unobstructed passage of one end of a suture from a suture package supported within receptacle 76 to finger 30 of load cell assembly 14. A cutout 92 may also be provided in a sidewall 94 of housing 74 to allow a suture to be connected directly to finger 30 of load cell assembly 14.

In use, a suture package is retained within receptacle 76 of jig 16 using clamp 82 or by a carrier member as discussed above. One end of a suture supported within the suture package is withdrawn from the suture package a distance sufficient to facilitate attachment of the end of the suture to finger 30 of load cell assembly 14. In one embodiment, finger 30 includes a notch for retaining the end of the suture. Alternately, other fastening techniques may be used to secure the suture to finger 30, e.g., tying, clips, etc. Next, suture package support member 72 may be pivoted about pivot member 75 in relation to base member 70 of jig 16 to selectively adjust the position of the suture package in relation to finger 30 of load cell assembly 14. By adjusting the position of the suture package in relation to finger 30 of load cell assembly 14, the angle of withdrawal of a suture from a suture package can be selected to approximate the probable angle or angles of suture withdrawal from a suture package by a surgeon or nurse.

After suture package support member 72 has been properly positioned, the drive mechanism is actuated to advance jig 16 including the suture package along track 60. Although illustrated as being linear, track 60 may be curved to simulate the exact motion of a surgeon or nurse during withdrawal of a suture from a suture package. As jig 16 is advanced along track 60 away from load cell assembly 14, the suture is withdrawn from the suture package. Withdrawal of the suture from the suture package creates strain in the suture which may vary as it is withdrawn. This strain is translated by the force measuring device of load cell assembly 14 into signals e.g., electrical, which are relayed by electrical cables to a display device 104 as is known in the art. The display device translates the signals into usable data indicative of the forces required to effect removal of the suture from the suture package. Suture pull out tester 10 measures the force required to effect removal of a suture from a suture package throughout the suture removal process. By determining the forces required to remove a suture from a suture package, design flaws in the construction of the suture package can be identified and, ideally, improved upon.

It will be understood that various modifications may be made to the embodiments disclosed herein. For example, the frame, although shown as a three dimensional rectangular structure, may be configured as any support structure capable of supporting the load cell assembly, the jig and the drive track assembly to achieve the desired purpose. Further, it is envisioned that the jig may assume a variety of different configurations capable of retaining a suture package thereon or therein. Moreover, the suture pull-out tester may be used to measure the withdrawal forces of other types of filaments, besides sutures, from filament packages. Therefore, the above description should not be construed as limiting, but merely as exemplifications of embodiments. Those skilled in the art will envision other modifications within the scope and spirit of the claims appended hereto.

What is claimed is:

1. A suture pull-out tester comprising:
   a load cell assembly including a force measuring device and an attachment member, the attachment member communicating with the force measuring device and being adapted to retain one end of a filament;
   a drive track;
   a jig movably supported on the drive track, the jig including a housing defining a receptacle configured to support a suture package; and
   a drive assembly associated with the jig, the drive assembly being operative to move the jig along the drive track such that when a suture package housing a filament is supported in the jig and the one end of the filament is retained by the attachment member, movement of the jig along the drive track withdraws the filament from the suture package such that the load cell assembly can measure the force required to effect removal of the filament from the suture package.

2. A suture pull-out tester according to claim 1, further including a frame, the frame supporting the load cell assembly, the drive track and the jig.

3. A suture pull-out tester according to claim 2, wherein the frame defines a three dimensional rectangular structure.

4. A suture pull-out tester according to claim 2, wherein the load cell assembly and the drive track are movably mounted on the frame to facilitate repositioning thereof.

5. A suture pull-out tester according to claim 2, wherein the frame includes first, second and third transverse beams, the load cell assembly being supported between the first and second transverse beams and the drive track being supported between the second and third transverse beams.

6. A suture pull-out tester according to claim 5, wherein the drive track and the load cell assembly are supported on runners, each of the runners being slidably supported on a respective one of the first, second and third transverse beams.

7. A suture pull-out tester according to claim 1, wherein the force measuring device includes a mechanical transducer.

8. A suture pull-out tester according to claim 7, wherein the mechanical transducer is a strain gauge.

9. A suture pull-out tester according to claim 1, wherein the force measuring device is connected to a display device.

10. A suture pull-out tester according to claim 2, wherein the load cell assembly is supported on a support block, the support block being supported on the frame.

11. A suture pull-out tester according to claim 1, wherein the drive assembly is fluid driven.

12. A suture pull-out tester according to claim 1, wherein the drive assembly includes a screw drive mechanism.

13. A suture pull-out tester according to claim 1, wherein the drive assembly includes an induction drive mechanism.

14. A suture pull-out tester according to claim 1, wherein the jig includes a base member movably supported on the drive track and a suture package support member supported on the base member.

15. A suture pull-out tester according to claim 14, wherein the suture package support member is pivotally mounted on the base member.

16. A suture pull-out tester according to claim 14, wherein the suture package support member defines the receptacle.

17. A suture pull-out tester according to claim 16, wherein the suture package support member further includes a clamp positioned within the receptacle to secure the suture package within the receptacle.

18. A suture pull-out tester according to claim 17, wherein the clamp is urged by a biasing member from a rear wall defining the receptacle towards a front wall defining the receptacle.

19. A suture pull-out tester according to claim 1, wherein the drive track is linear.

20. A suture pull-out tester according to claim 1, wherein the drive track is non-linear.

21. A method for measuring the forces required to withdraw a suture from a suture package, the method comprising the following steps:
   i) providing a suture pull-out tester including a load cell assembly having a force measuring device and an attachment member, a drive track, a jig and a drive assembly for advancing the jig along the drive track;
   ii) supporting a suture package on the jig;
   iii) attaching one end of a filament supported within the suture package to the attachment member of the load cell assembly;
   iv) actuating the drive assembly to advance the jig along the drive track to withdraw the suture from the suture package at a controlled rate; and
   v) using the force measuring device of the load cell assembly to measure the tension in the filament during withdrawal of the filament from the suture package.

22. A method according to claim 21, wherein the step of providing includes providing a force measuring device in the form of a strain gauge.

23. A method according to claim 21, wherein the step of providing includes providing a display device for translating signals from the force measuring device into usable data.

* * * * *